United States Patent
Hoshikawa et al.

(10) Patent No.: US 6,797,048 B2
(45) Date of Patent: Sep. 28, 2004

(54) METHOD FOR PREPARING GLASS-CERAMIC

(75) Inventors: Takeshi Hoshikawa, Kami-gun (JP);
Masatoshi Yamazoe, Kami-gun (JP);
Hirohisa Yamamoto, Osaka (JP);
Teruo Anraku, Osaka (JP)

(73) Assignee: Yamamoto Precious Metal Co., Ltd., Osaka (JP)

( * ) Notice: Subject to any disclaimer, the term of this patent is extended or adjusted under 35 U.S.C. 154(b) by 22 days.

(21) Appl. No.: 10/169,066
(22) PCT Filed: Jan. 5, 2001
(86) PCT No.: PCT/JP01/00021
§ 371 (c)(1),
(2), (4) Date: Jul. 3, 2002
(87) PCT Pub. No.: WO01/49632
PCT Pub. Date: Jul. 12, 2001

(65) Prior Publication Data
US 2003/0056692 A1 Mar. 27, 2003

(30) Foreign Application Priority Data
Jan. 7, 2000 (JP) ........................................ 2000-001659

(51) Int. Cl.[7] .......................... C04B 35/19; C04B 35/64; A61K 6/27; C03C 3/04
(52) U.S. Cl. ............................. 106/35; 433/215; 501/2; 501/3; 501/4; 501/14; 501/16; 501/21; 501/24; 521/25
(58) Field of Search ................. 106/35, 3; 501/2, 501/3, 4, 14, 16, 21, 24, 25, 6, 32; 433/215, 201.1, 212.1, 202.1, 218, 220; 65/33.7; 428/325, 323, 701, 702, 697, 699, 426, 428

(56) References Cited

U.S. PATENT DOCUMENTS
4,604,366 A * 8/1986 Kacicz et al.
4,798,536 A * 1/1989 Katz (List continued on next page.)

FOREIGN PATENT DOCUMENTS
| | | |
|---|---|---|
| EP | 1253116 | * 10/2002 |
| JP | 49-8921 | 3/1974 |
| JP | 52-5047 | 2/1977 |
| JP | 55-40546 | 10/1980 |
| JP | 60-112644 | 6/1985 |
| JP | 10-036136 | 2/1998 |
| JP | 10-094550 | 4/1998 |

OTHER PUBLICATIONS

*Perspectives in Dental Ceramics;* "Low Fusing Porcelains" (Derek W. Jones); Quintessence Publishing Co., Chicago, Illinois (1988); pp 29–64.

Hoshikawa et al "Inversion Temperature and Thermal Expansion of Leucite Formed in the System $SiO_2$–$Al_2O_3$–$K_2O$–$Na_2O$"; Osaka Municipal Technical Research Inst. vol. 60(9)(351–355), (1986); pp 17–21.

*Dental Ceramics;* "The Chemical and Physical Properties of Dental Porcelain" (David Binns); Quintessence Publishing Co., Chicago, Illinois (1983); pp 41–82.

Hoshikawa et al "Formation of Leucite and Thermal Expansion in $SiO_2$–$Al_2O_3$–$K_2O$–$Na_2O$"; Osaka Municipal Technical Research Inst. vol. 80(1) pp 36–48 (1972).

International Search Report dated Apr. 2, 2001.

*Primary Examiner*—Archene Turner
(74) *Attorney, Agent, or Firm*—Armstrong, Kratz, Quintos, Hanson & Brooks, LLP (57) ABSTRACT

The present invention provides a method for preparing a glass-ceramic containing leucite crystals, comprising the steps of: mixing (1) a glassy material comprising 53 to 65 wt. % of $SiO_2$, 13 to 23 wt. % of $Al_2O_3$, 9 to 20 wt. % of $K_2O$ and 6 to 12 wt. % of $Na_2O$ and (2) synthetic leucite seed crystals comprising 53 to 64 wt. % of $SiO_2$, 19 to 27 wt. % of $Al_2O_3$ and 17 to 25 wt. % of $K_2O$, and heat-treating the mixture at 750 to 950° C. for 1 to 5 hours; and a dental porcelain powder and a metal-ceramic restoration both comprising a glass-ceramic prepared by the method. The porcelain comprising the glass-ceramic prepared by the method is substantially free of opacification and decrease in the coefficient of thermal expansion, during fusion-bonding to a metal frame.

11 Claims, 1 Drawing Sheet

U.S. PATENT DOCUMENTS

| | | | |
|---|---|---|---|
| 4,978,640 A | * 12/1990 | Kelly | |
| 5,071,801 A | 12/1991 | Bedard et al. | 501/128 |
| 5,653,791 A | * 8/1997 | Panzera et al. | |
| 5,698,019 A | * 12/1997 | Frank et al. | |
| 5,705,273 A | * 1/1998 | Denry et al. | |
| 5,994,246 A | * 11/1999 | Denry | |
| 6,133,174 A | * 10/2000 | Brodkin et al. | |

* cited by examiner

METHOD FOR PREPARING GLASS-CERAMIC

TECHNICAL FIELD

The present invention relates to a method for preparing a glass-ceramic. The pulverized glass-ceramics (glass-ceramic powders) obtained by the method of the invention is useful particularly as a porcelain to be built up and fused for coating the surface of a metal frame and thereby fabricating a dental prosthesis with excellent aesthetic qualities.

BACKGROUND ART

A technique is known in which a porcelain powder (hereinafter referred to simply as "porcelain") comprising a glass-ceramic is built up on and fusion-bonded to the surface of a metal frame to fabricate a dental prosthesis which has an appearance similar to natural teeth and high mechanical and chemical durability. The metal frame is mainly made of a precious metal alloy which has an approximately constant coefficient of thermal expansion (about $(14.2\pm0.5)\times10^{-6}/°C$.).

In such dental prosthesis fabrication, a coating process comprising building up, fusion-bonding and cooling a porcelain on the metal frame surface is repeated several times to form the external shape of the dental prosthesis. Stated more specifically, the fabrication includes the basic steps of forming three layers by sequentially building up and fusion-bonding an undercoat opaque for concealment of the metal color and fusion bonding, a dentine porcelain that determines the basic color of the prosthetic teeth, and an enamel porcelain that reproduces the characteristics of tooth enamel. In addition, the fabrication involves the step of forming a margin that matches with natural teeth, and adjusting steps such as coloring, color tone modification and the like. Thus, in the known technique, the coating process comprising building up, fusion-bonding and cooling a porcelain on a metal frame is repeated at least 3 times, up to about 10 times.

Therefore, the porcelains are required to have a coefficient of thermal expansion approximating that of the material of the metal frame and have thermal stability such that their coefficients of thermal expansion scarcely change during the repeated coating process.

Leucite crystals are represented by the chemical formula $4SiO_2.Al_2O_3.K_2O(=KAlSi_2O_6)$. Since leucite crystals have a large coefficient of thermal expansion, a glass-ceramic containing a specific amount of leucite crystals has a coefficient of thermal expansion approximately equal to that of the material of the metal frame. Further, when the leucite crystal phase coexists with a glass matrix phase, the two phases as a whole have uniform light transmittance (transparency) because the refractive indices of the two phases are close to each other. Therefore, addition of a coloring ingredient to a porcelain comprising the coexisting mixture enables desired coloration of a restored dental prosthesis to impart a highly aesthetic appearance similar to the appearance of natural teeth. Because of these excellent characteristics (coefficient of thermal expansion and transparency) of leucite crystal-containing glass-ceramics, the use of leucite crystal-containing glass-ceramics as materials (porcelains) for coating metal frames has been proposed.

For example, U.S. Pat. No. 4,604,366 discloses a method for preparing a ceramic porcelain, comprising blending a matrix glass with several types of leucite crystal-containing glass-ceramic frits having different leucite crystal contents and different coefficients of thermal expansion. However, this method necessitates troublesome procedures for determining the ratio of the at least three types of ingredients and blending these ingredients, in order to suitably control the leucite crystal content and coefficient of thermal expansion of the final product porcelain. Moreover, the dental prosthesis obtained by firing the ceramic porcelain has the serious problem of non-uniform leucite crystal distribution.

U.S. Pat. No. 4,798,536 discloses a method for preparing a ceramic porcelain, comprising mixing a natural feldspar, such as Wyoming feldspar, as a leucite crystal origin point with a glass matrix-forming ingredient, and melting, slowly cooling and then suddenly cooling the mixture. However, this method includes troublesome procedures for purifying the natural feldspar, and is complicated as a whole. In addition, trace impurities derived from the natural feldspar are liable to remain in the porcelain and decrease the transparency, thereby deteriorating the color of the resulting dental prosthesis.

When a porcelain is fusion-bonded to a metal frame, a lower fusion-bonding temperature is desirable from a workability point of view. However, the leucite crystal phase is instable in "low-fusing porcelain" which is softened and fluidized at 750 to 950° C. and fusion-bonded to a metal surface. Thus, if the porcelain is maintained at 950° C. or lower, the leucite crystal phase undergoes transformation to a different type of crystal phase, or shifts to a state of coexistence with a different type of crystal phase. More specifically, when a powder of a known low-fusing, leucite crystal-containing glass-ceramic (a composite of leucite crystals and matrix phase) is fired at 750 to 950° C. to coat a metal frame, Na—K feldspathic crystals (high temperature-type Na—K sanidine) start to precipitate after a given period of time, and then the leucite crystals begin to decrease and finally disappear, since the leucite crystals contained are a metastable crystal phase. The precipitation of the Na—K feldspathic crystals lowers the coefficient of thermal expansion and causes opacification in the glass-ceramic. Thus, the coefficient of thermal expansion of the glass-ceramic gradually decreases during the repeated coating process comprising building up, fusion-bonding and cooling of the glass-ceramic on a metal frame. As a result, the glass-ceramic has defects such as cracks owing to the stress of strain between the frame material and the ceramic coating layer, leading to low adhesion between the frame material and the ceramic coating layer. Further, the opacification of the glass-ceramic impairs the transparency of the ceramic coating layer.

In the above situation, the development of a novel porcelain which can be easily prepared and is free of deterioration in characteristics (i.e., decrease in the coefficient of thermal expansion, or opacification) during a process of coating a metal frame is desired.

DISCLOSURE OF THE INVENTION

An object of the present invention is to provide a leucite crystal-containing glass-ceramic which can be easily prepared.

Another object of the invention is to provide a leucite crystal-containing glass-ceramic whose leucite crystal content does not substantially change when heated, and which exhibits a stable coefficient of thermal expansion and excellent transparency, and a porcelain comprising a powder of the glass ceramic.

A further object of the invention is to provide a leucite crystal-containing glass-ceramic porcelain in which the leucite crystals, once precipitated, do not substantially decrease in amount during the process of coating a metal frame.

A further object of the invention is to provide a porcelain in which crystals of types other than leucite crystals (e.g., Na—K feldspathic crystals) do not substantially precipitate during the process of coating a metal frame, in other words, to provide a leucite crystal-containing glass-ceramic porcelain in which crystals of types other than leucite crystals (e.g., Na—K feldspathic crystals) begin to precipitate sufficiently long after the precipitation of leucite crystals reaches the saturation point.

A further object of the invention is to provide a leucite crystal-containing glass-ceramic porcelain which is free of opacification and decrease in the coefficient of thermal expansion during the process of coating a metal frame with the porcelain.

A further object of the invention is to provide a dental prosthesis obtainable by building up and fusion-bonding the leucite crystal-containing glass-ceramic porcelain onto the surface of a metal frame.

The above objects of the invention can be achieved by mixing a glassy material and leucite crystals (seed crystals) previously synthesized, and then heat-treating the resulting mixture under specific conditions.

Specifically, the present invention provides a method for preparing a leucite crystal-containing glass-ceramic, comprising the steps of:
mixing
(1) a glassy material comprising 53 to 65 wt. % of $SiO_2$, 13 to 23 wt. % of $Al_2O_3$, 9 to 20 wt. % of $K_2O$ and 6 to 12 wt. % of $Na_2O$, and
(2) synthetic leucite seed crystals comprising 53 to 64 wt. % of $SiO_2$, 19 to 27 wt. % of $Al_2O_3$ and 17 to 25 wt. % of $K_2O$; and heat-treating the mixture at 750 to 950° C. for 1 to 5 hours.

The glassy material (1) for use in the invention comprises $SiO_2$, $Al_2O_3$, $K_2O$ and $Na_2O$ as essential components. $Na_2O$ is a component which lowers the fusing point of the glassy material (1).

The glassy material (1) may contain optional components which does not prevent precipitation of leucite crystals or inhibit the transparency of the glass-ceramic, such as F and colorless oxides of Li, Mg, Ca, Sr, B, P, Ti, Zr, etc. Specific examples of optional components include $Li_2O$ (2 wt. % or less), MgO (3 wt. % or less), CaO (3 wt. % or less), SrO (2 wt. % or less), $B_2O_3$ (3 wt. % or less), $P_2O_5$ (2 wt. % or less), $TiO_2$ (3 wt. % or less), $ZrO_2$ (1 wt. % or less) and F (2 wt. % or less). It is preferable that the total proportion of these optional component(s) in the glassy material (1) be 6 wt. % or less.

The concomitant use of the optional components accomplishes the following effects. Oxides of Li, Mg, Ca, Sr, B, P, Ti or the like are effective for lowering the fusing point of the glass-ceramic. Oxides of Mg, Ca, Sr, B, Ti or the like improve the water resistance and acid resistance of the glass-ceramic. Oxides of Mg, Ca, Sr, Ti, Zr or the like improve the alkali resistance of the glass-ceramic.

In this specification and the appended claims, when an expression such as, for example, "comprising 2 wt. % or less", is used to indicate an oxide content, it includes the case where no oxide is contained.

More preferably, the glassy material (1) comprises about 61 to 65 wt. % of $SiO_2$, about 12 to 20 wt. % of $Al_2O_3$, about 10 to 15 wt. % of $K_2O$, about 6 to 10 wt. % of $Na_2O$, 0.3 wt. % or less of $Li_2O$, 1.0 wt. % or less of MgO, 2 wt. % or less of CaO, about 0.3 to 1.5 wt. % of $B_2O_3$, 1 wt. % or less of SrO, 2 wt. % or less of $TiO_2$, 0.5 wt. or less of $ZrO_2$, 0.5 wt. % or less of $P_2O_5$ and 1.5 wt. % or less of F. In the glassy material having the above composition, the total proportion of the optional components is preferably 6 wt. % or less.

The glassy material (1) can be prepared by a known melting process, for example by melting a starting mixture comprising predetermined proportions of components such as oxides, hydroxides, carbonates or the like, at about 1550 to 1750° C. for about 2 to 5 hours, more preferably at 1600 to 1700° C. for about 3 to 4 hours. The starting mixture can be melted in a conventional crucible such as a high alumina crucible, a platinum crucible, an Rh-containing platinum crucible, a Zr-containing platinum crucible or the like. Among them, an Rh-containing platinum crucible and Zr-containing platinum crucible are more preferable.

In producing the glass-ceramic, the glassy material (1) is preferably used in powder form. A powder of the glassy material (1) can be prepared, for example, in the following manner: a molten glass obtained by the above melting process is poured into water, or a crucible containing the molten glass is placed in water, to suddenly cool and coarsely crush the molten glass. The glassy portion is then separated, collected, dried and pulverized to a predetermined size (a particle size distribution with usually 200 mesh or smaller (=about 75 um or smaller), more preferably a mean particle size of about 30 to 60 $\mu$m), using a roll mill, ball mill, jet mill or like pulverizer, optionally followed by sieving.

In the invention, the synthetic leucite seed crystals (2) for use as seed crystals may be synthetic leucite crystals having a theoretical composition, a leucite solid solution containing $SiO_2$ dissolved therein, synthetic leucite crystals in which a part (5% or less) of K is substituted by Rb, or a mixture of at least two of these types of leucite crystals. When the synthetic leucite seed crystals (2) are used in a mixture form, the mixing ratio of each component is not limited. Preferably, synthetic leucite crystals having a theoretical composition are used as seed crystals.

The synthetic leucite seed crystals (2) for use in the invention comprise $SiO_2$, $Al_2O_3$ and $K_2O$ as essential components. The synthetic leucite seed crystals (2) may contain optional component(s) which neither decrease(s) the leucite crystal content to 80 wt. % or less, nor reduce(s) the transparency. Such optional components include F and oxides of Li, Na, Mg, Ca, Sr, B, P, Ti, Zr, etc. These optional components reduce a crystallinity in the seed crystals and thus cannot be used in large proportions, but promote diffusion of the essential components and achieve a lower melting point of the essential components while melting. A preferable total content of the optional component(s) in the synthetic leucite crystal seed (2) is 3 wt. % or less.

More preferably, the synthetic leucite seed crystals (2) comprise about 53 to 56 wt. % of $SiO_2$, about 22 to 25 wt. % of $Al_2O_3$ and about 20 to 25 wt. % of $K_2O$.

The synthetic leucite seed crystals (2) are not limited, but may be prepared by a conventional melting process similar to the process for preparing the glassy material (1). For example, a starting mixture comprising predetermined proportions of oxides, hydroxides, carbonates or the like is melted at 1700° C. or higher (more preferably about 1750° C.) for at least 2 hours (more preferably about 3 hours), slowly cooled to about 1300° C. at a cooling rate of about 100° C./hr or slower (more preferably about 50° C./hr) to complete crystallization, and then allowed to cool to room temperature (about 15 to 25° C.), thereby giving synthetic leucite crystals. The formation of synthetic leucite crystals can be easily confirmed by powder X-ray diffraction analysis of the product. In the above slow cooling process, it is preferable that, at an intermediate stage of the slow cooling, the melt is maintained for example at 1400 to 1500° C. for about 2 to 3 hours. The starting mixture can be melted in a conventional crucible such as a high alumina crucible, a platinum crucible, an Rh-containing platinum crucible, a Zr-containing platinum crucible or the like.

Alternatively, the synthetic leucite seed crystals (2) can be synthesized by placing the above starting mixture in a crucible and maintaining the mixture at a temperature not lower than 1400° C. for a given period of time for firing. In this case, the higher the firing temperature is, the shorter time the synthesis requires. For example, when the firing temperature is about 1600° C., the mixture is maintained for about 5 hours to obtain seed crystals with a crystallinity of about 95%. In contrast, when the firing temperature is about 1400° C., the mixture needs to be maintained for about 3 to 6 days to obtain seed crystals having the same degree of crystallinity as above.

Preferably, in production of the glass-ceramic, the synthetic leucite seed crystals (2) are also used in pulverized form. A powder of the synthetic leucite seed crystals (2) can be obtained for example as follows: the crucible containing the high-temperature synthetic leucite crystals prepared in the above manner is placed in water to suddenly cool and coarsely crush the crystals, and the crystals are separated, collected, dried and then pulverized to a predetermined size (usually a particle size distribution with 200 mesh or smaller (=about 75 μm or smaller), more preferably a mean particle size of about 30 to 60 μm) using a pulverizer such as a roll mill, ball mill, jet mill or the like, optionally followed by sieving. Note that the synthetic leucite seed crystals (2) may be of any size and are not limited to the above sizes, as long as they function as seed crystals. For example, the use of leucite crystals in the form of fine powder with a mean particle size of about 3.5 μm achieves desired effects.

In producing the glass-ceramic of the invention, a starting mixture is used which comprises, per 100 parts by weight of a powder of the glassy material (1), 0.5 to 3 parts by weight of a powder of the leucite seed crystals (2) with a high purity synthesized in the above manner. The use of an excess amount of the leucite seed crystals (2) leads to opacification of the glass-ceramic, and thus is undesirable.

The proportion of the synthetic leucite seed crystals (2) to the glassy material (1) is more preferably 1 to 2 parts by weight per 100 parts by weight of the glassy material (1). When using these ingredients in such proportions, a glass-ceramic can be obtained which has further improved characteristics.

The glass-ceramic of the invention can be prepared by heat-treating the above mixture usually at about 750 to 950° C. for about 1 to 5 hours, more preferably at about 800 to 900° C. for about 3 to 5 hours.

When the glass-ceramic of the invention is used as, for example, a porcelain, the glass-ceramic is made into a powder by a conventional pulverizing process, or into a controlled particle size powder by sieving the powder. The powder for use as a porcelain is not limited, but usually has a particle size of 100 μm or smaller. More preferably, the powder has a mean particle size of 5 to 50 μm and contains 1% or less of fine particles with a particle size of 1 μm or smaller.

If the glassy material (1) alone (without the synthetic leucite seed crystals) is heat-treated, the results are as follows: Even when the glassy material (1) alone is heat-treated, leucite crystals form and slowly grow. This is presumably because the edges of the pulverized glassy material, or trace amounts of high-melting inorganic impurities (fine particles of $Al_2O_3$, $SiO_2$ or the like mixed in during pulverization) serve as crystal nuclei. However, when the leucite crystal growth depends on such crystal nuclei formed spontaneously, a long period of time is required for the leucite crystals in the glass phase to grow and reach the saturation point. At the time when the leucite crystals reach the saturation point, the glass-ceramic having a desired coefficient of thermal expansion is formed. At that time, however, different types of crystals such as Na—K feldspathic crystals (stable phases) have begun to precipitate. Therefore, it is impossible to effectively prevent the decrease in the coefficient of thermal expansion (i.e., opacification) of the glass-ceramic.

On the other hand, the starting mixture for use in the invention contains a specific amount of synthetic leucite seed crystals (2), so that, in the glass phase under heated conditions, leucite crystals rapidly grow and reach the saturation point in a short time. Accordingly, when the resulting glass-ceramic is used as a porcelain, there is a sufficiently long period of time before different types of crystals such as Na—K feldspathic crystals begin to precipitate. As a result, even when the glass-ceramic is used as a porcelain under high temperature conditions, the leucite crystals remain stable and the opacification owing to precipitation of different types of crystals (feldspars) is effectively inhibited.

An excessive proportion of the synthetic leucite seed crystals (2) in the starting mixture used in the invention causes the following problems: When the powder mixture of the glassy material (1) and leucite crystals (2) is heat-treated for sinter-crystallization, the glassy material (1) powder and seed crystal (2) powder are not fully fusion-bonded to each other and leave minute voids, leading to opacification. Moreover, when the glass-ceramic porcelain powder is fusion-bonded onto a metal frame, it is difficult to degas the porcelain, resulting in formation of fine cracks in the fusion-bonded object, which is not practical.

The leucite crystals in the glass-ceramic obtained by the method according to the invention have a particle size up to 200 mesh (up to about 75 μm). It is thus apparent that leucite crystals derived from the seed crystals (2) maintain their original particle size. On the other hand, leucite crystals which have grown using the seed crystals (2) as the crystal origin point have a mean particle size of about 5 μm or smaller, mainly because (a) they grow from a number of pieces of crystal origin point, and (b) the crystal growth rate is low since the heat treatment for crystal growth is carried out at a low temperature of 750 to 950° C. Accordingly, there is a state that creates a tensile stress between the leucite crystal phase (coefficient of thermal expansion $\alpha$=about $22 \times 10^{-6}$/° C.) and the matrix glass phase ($\alpha$=about $9 \times 10^{-6}$/° C.) in the glass-ceramic obtained by crystallization treatment, owing to the difference between the coefficients of thermal expansion of the two phases. When this ceramic-glass is pulverized, portions with larger tensile stress, i.e., portions in which the particle size of leucite crystals is larger, are selectively crushed. As a result, even when the glass-ceramic porcelain powder has a particle size up to 200 mesh (up to about 75 μm), the leucite crystal particles with a large particle size derived from the seed crystals (2) are remarkably decreased.

The glass-ceramic obtained by the invention contains leucite crystals, and has a coefficient of thermal expansion of (12 to 17.5)$\times 10^{-6}$/° C. at 50 to 500° C. The glass-ceramic of the invention has the characteristic that, even if heat-treated under severe conditions (at 850° C. for 3 hours or at 750° C.

for 10 hours), the glass-ceramic is substantially free of reduction in leucite crystal content or precipitation of different types of crystals such as Na—K feldspathic crystals.

The leucite crystals in the glass-ceramic obtained by the method of the invention may be leucite crystals having a theoretical composition, a leucite solid solution containing a $SiO_2$ component dissolved therein, leucite crystals in which a part (2% or less) of K is substituted by Rb, or a mixture containing at least two of these types of crystals.

In the glass-ceramic obtained by the invention, leucite crystals in an amount equal or close to the saturation amount at the crystal growth temperature during the production of the glass ceramic are uniformly dispersed as a metastable crystal phase having a mean particle size of 10 μm or smaller (more preferably 5 μm or smaller).

The leucite crystal content in the glass-ceramic according to the invention is about 15 to 43 wt. %, although depending on the proportions of the glassy material (1) and the synthetic leucite seed crystals (2), heat treatment conditions in producing the glass-ceramic, or other factors.

When a powder or a controlled particle size powder of the glass-ceramic according to the invention is used as a porcelain, any known additives such as opacifiers, coloring pigments, fluorescent materials or the like may be added as required, as long as they do not inhibit the effects of the invention.

Useful opacifiers include, for example, rutile or anatase $TiO_2$, $SnO_2$, $ZrSiO_4$, $CeO_2$, and stabilized $ZrO_2$ (stabilizer= $Y_2O_3$, CaO, MgO or the like).

Examples of coloring pigments include $Fe_2O_3$ pigments, $Fe_2O_3$—$Cr_2O_3$ pigments, $Fe_2O_3$—CoO—$Cr_2O_3$ pigments, $PrO_2$ pigments, $V_2O_5$ pigments, CeO pigments, $MnO_2$ pigments and $SnO_2$—$Cr_2O_3$ pigments.

Examples of fluorescent materials include Ce-doped $Y_2O_3$.

The porcelain mixture containing specific additives is kneaded in a routine manner using water, modeling liquid (e.g., aqueous PVA solution), and then applied to or built up on a metal frame. To improve the workability, a known paste-form kneading agent (such as polyethylene glycol dimethyl ether, polyethylene glycol with a specific degree of polymerization, or the like) may be added to make the porcelain mixture into a paste.

When the glass-ceramic powder according to the invention is used as a porcelain for dental prosthesis fabrication, the powder can be used by the same method as for known porcelains. For example, a coating process consisting of building up, fusion-bonding and cooling the porcelain on the surface of a metal frame is repeated several times to form the external shape of dental prosthesis. The glass-ceramic according to the invention undergoes no substantial change in leucite crystal content when fired and thus has a substantially constant coefficient of thermal expansion, even after the glass-ceramic is subjected to 10 cycles, each consisting of (i) vacuum firing defined in JIS T 6515 (manufacturer's specific process) and (ii) placing the glass-ceramic in a furnace at a predetermined temperature (for example 600° C.), vacuumizing the furnace, then raising the temperature in the furnace to 900° C. at a rate of 60° C./min, and taking out the glass-ceramic and allowing it to cool in the atmosphere (total firing time=about 1 hour). Further, the fired body obtained in the above manner is highly transparent since precipitation of different types of crystals such as Na—K feldspathic crystals is inhibited. Therefore, the glass-ceramic obtained according to the invention is extremely useful as a porcelain for use on a dental metal frame.

Preferably, the metal frame is made of a known precious metal alloy. Examples of precious metal alloys include high karat golds, medium karat golds, gold-silver-palladium alloys, gold-palladium alloys and silver-palladium alloys.

In building up and fusion-bonding a powder of the glass-ceramic of the invention onto the metal frame, an undercoat porcelain is used to conceal the metal color. As the undercoat porcelain, a glass-ceramic powder containing an opacifier (alias "opaque porcelain") or a kneaded paste thereof (alias "paste opaque") is preferably used. As a topcoat porcelain formed to imitate natural teeth (alias "dentine" or "enamel"), a glass-ceramic powder containing a coloring pigment (which may optionally contain a small amount of opacifiers) is preferably used.

BEST MODE FOR CARRYING OUT THE INVENTION

The following Examples are provided to illustrate the features of the present invention in further detail.

Table 1 shows the compositions (wt. %) of the glassy material (1) and of the synthetic leucite seed crystals (2) with high purity used in the following Examples and Comparative Examples.

TABLE 1

| Component | Glassy material (1) | | | | | | Leucite seed crystals (2) | |
|---|---|---|---|---|---|---|---|---|
| | G1 | G2 | G3 | G4 | G5 | G6 | L1 | L2 |
| $SiO_2$ | 64.1 | 63.9 | 65.3 | 63.6 | 63.8 | 61.7 | 55.1 | 55.1 |
| $Al_2O_3$ | 15.0 | 15.1 | 15.0 | 15.0 | 14.7 | 15.0 | 23.3 | 23.3 |
| $K_2O$ | 10.3 | 10.5 | 11.0 | 10.8 | 10.9 | 12.2 | 21.6 | 21.6 |
| $Na_2O$ | 8.5 | 8.4 | 6.6 | 8.5 | 8.5 | 9.0 | — | — |
| MgO | 0.3 | 0.3 | 0.3 | 0.3 | 0.3 | 0.3 | — | — |
| CaO | 1.2 | 1.2 | 1.2 | 1.2 | 1.2 | 1.2 | — | — |
| $B_2O_3$ | 0.6 | 0.6 | 0.6 | 0.6 | 0.6 | 0.6 | — | — |
| Particle size | <75 μm | <75 μm | <75 μm | <75 μm | <75 μm | <75 μm | <75 μm | 3.5 μm (average) |

EXAMPLE 1

Glassy material sample G1 (99 parts by weight) and leucite seed crystal sample L1 (1 part by weight) shown in Table 1 were uniformly mixed together, heat-treated at 850° C. for a given period of time ranging from 1 hour to 24 hours for crystallization, cooled and pulverized to obtain glass-ceramic powders according to the present invention.

The obtained glass-ceramic powders had a leucite crystal content ranging from 0 to 20.5 wt. %, and the leucite crystals had mean particle sizes of 5 $\mu$m or smaller.

Comparative Example 1

Glass-ceramic powders were prepared by following the procedure of Example 1 except that the leucite seed crystals were not used. Specifically, 100 parts by weight of glassy material sample G1 was heat-treated at 850° C. for a given period of time ranging from 1 to 24 hours, cooled, pulverized to obtain comparative glass-ceramic powders.

The obtained glass-ceramic powders had a leucite crystal content ranging from 0 to 18 wt. %, and the leucite crystals had mean particle sizes of 5 $\mu$m or smaller.

Test Example 1

The glass-ceramic powders obtained in Example 1 and Comparative Example 1 were molded in a biaxial press. The molded bodies (6 mm×6 mm×25 mm) were placed in a vacuum furnace at 600° C., and then the pressure in the furnace was reduced to about 6.7 kPa. Subsequently, the molded bodies were heated to 900° C. at a rate of 60° C./min and maintained at the same temperature for 1 minute for firing. The pressure in the furnace was raised to atmospheric pressure, and the fired bodies were cooled to about 600° C. in the furnace and then allowed to cool outside the furnace. In the following Table 2, "after 4 times of refiring" means "after subjecting a vacuum-fired body obtained by following the above firing schedule to a similar firing schedule (without the reduction of pressure) four times". As used hereinafter, the term "4-time refired body" means a body obtained by firing a vacuum-fired body four times.

The coefficients of thermal expansion (the average of the values obtained at temperatures from 50 to 500° C.) of the obtained vacuum-fired bodies and 4-time refired bodies were measured using a thermal dilatometer.

Figure 1:
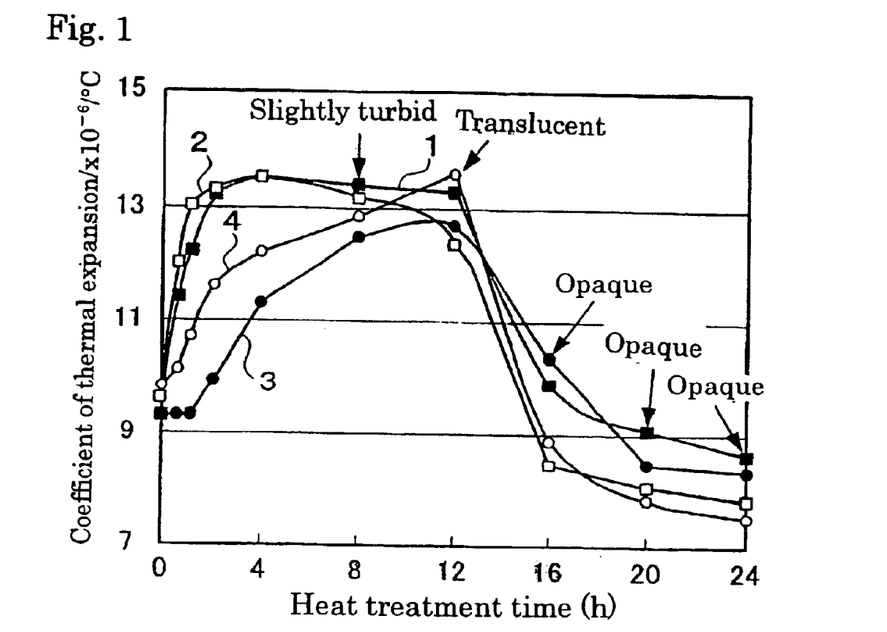
FIG. 1 is a graph showing the relationship between the heat treatment time for crystallization and the coefficient of thermal expansion in the fired bodies of the glass-ceramic powders obtained in Example 1 and Comparative Example 1.

FIG. 1 is a graph representing the relationship between the crystallization heat treatment time (h) of each glass-ceramic and the coefficient of thermal expansion (×10$^{-6}$/° C.) of each fired body, in vacuum-fired bodies prepared using the glass-ceramic powders obtained in Example 1 and Comparative Example 1 as starting materials and 4-time refired bodies thereof. As mentioned above, the temperature for crystallization heat treatment was 850° C.

FIG. 1 reveals that, in the vacuum-fired bodies of the glass-ceramic powders obtained in Example 1 (Curve 1), the coefficient of thermal expansion was nearly reached the maximum (13.3×10$^{-6}$/° C.) in 2 hours of the heat treatment at 850° C., and maintained the same value to the point where the heat treatment time was 8 hours. As the heat treatment was increased to 12 hours, the coefficient of thermal expansion was sharply decreased to a value less than the coefficient of thermal expansion of the glassy body before the crystallization heat treatment (9.3×10$^{-6}$/° C.).

Also in the 4-time refired bodies of the glass-ceramic powders obtained in Example 1 (Curve 2), the coefficient of thermal expansion changed slightly as the heat treatment time increased from 2 to 8 hours.

From the results obtained in the vacuum-fired bodies of glass-ceramic powders prepared by crystallization heat treatment at 850° C. and 4-time refired bodies thereof, it is apparent that the leucite crystal content (the corresponding coefficient of thermal expansion) in the porcelain according to the invention does not substantially change in the above firing schedule (which is the same as the actual firing schedule for porcelains).

In contrast, in the vacuum-fired bodies of the glass-ceramic powders obtained in Comparative Example 1 (Curve 3), the increase in the coefficient of thermal expansion owing to the heat treatment was small, and the coefficient of thermal expansion increased only to 12.3×10$^{-6}$/° C. in 8 hours of the heat treatment. Moreover, the vacuum-fired bodies had slight turbidity at that point, and were translucent when the coefficient of thermal expansion reached 12.7×10$^{-6}$/° C.

Further, in the 4-time refired bodies obtained using the glass-ceramic powders of Comparative Example 1 (Curve 4), the coefficient of thermal expansion greatly changed.

It is clear from the above results that in a glass-ceramic obtained by adding a leucite crystal powder as seed crystals to a glassy material and heat-treating the mixture for crystallization under specific conditions, the coefficient of thermal expansion increases to a desired value in a short period of time and is maintained at the desired high value for a long period of time. As a result, there is a long period of time before turbidity or opacification occurs.

Figure 2:
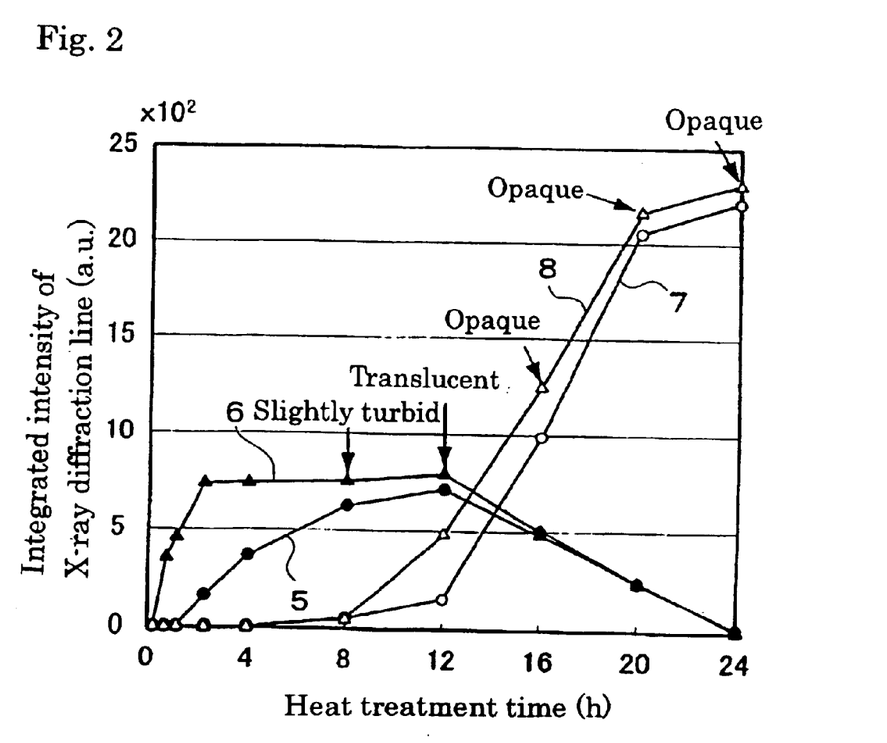
FIG. 2 is a graph showing the relationship between the heat treatment time for crystallization and the integrated intensity of X-ray diffraction line in the fired bodies of the above two types of glass-ceramic powders.

FIG. 2 is a graph showing the relationship between the heat treatment time (h) and the integrated intensity (a.u.) of X-ray diffraction line of each glass-ceramic fired body, in the case of vacuum-firing the glass-ceramic powders obtained in Example 1 and Comparative Example 1 by following the same firing schedule as described above.

In FIG. 2, Curve 5 represents the intensity of X-ray diffraction line ($d_{211}$) from leucite in the fired bodies of the glass-ceramic powders prepared in Comparative Example 1; Curve 6 represents the intensity of X-ray diffraction line ($d_{211}$) from leucite in the fired bodies of glass-ceramic powders prepared in Example 1; Curve 7 represents the intensity of X-ray diffraction line ($d_{130}$) from high temperature-type Na—K sanidine crystals in the fired bodies of the glass-ceramic powders prepared in Comparative Example 1; and Curve 8 represents the intensity of X-ray diffraction line ($d_{130}$) from high temperature-type Na—K sanidine crystals in the fired bodies of glass-ceramic powders prepared in Example 1.

FIGS. 1 and 2 reveal the following.

The increase in the coefficient of thermal expansion shown in FIG. 1 corresponds to the increase in leucite crystal content in the glass. Specifically stated, when no seed crystals are present (FIG. 2; Curve 5), leucite crystals begin to precipitate after an induction period of about 1 hour. On the other hand, when the seed crystals are added (FIG. 2; Curve 6), leucite crystals immediately begin to precipitate without an induction period, and the precipitation of the crystals reaches the saturation point in a short period (about 2 hours) of the heat treatment (in the corresponding Curve 1 in FIG. 1, the coefficient of thermal expansion nearly reaches the maximum).

Further, as seen from the graph in FIG. 2 (see Curve 7 relating to Comparative Example 1 and Curve 8 relating to Example 1), high temperature-type Na—K sanidine crystals begin to precipitate after an induction period of about 8 hours, and accordingly notable turbidity and opacification occur in the crystallized glass-ceramic (see Curve 5 relating to Comparative Example 1 and Curve 6 relating to Example 1). Similarly, it is understood that, in Curve 1 in FIG. 1, the glass-ceramics obtained by long-time crystallization heat treatment have a coefficient of thermal expansion lower than that of the glass without heat treatment ($9.3 \times 10^{-6}/°$ C.) because of the low thermal expansion properties of the precipitated high temperature-type Na—K sanidine crystals.

The above matters reveal the following:

(a) High temperature-type Na—K sanidine crystals, which usually cause opacification in a glass-ceramic of the above type, behave as an apparently stable crystal phase under the heat treatment conditions employed in Test Example 1.

(b) In contrast, leucite crystals, which are effective in maintaining the transparency of the glass-ceramics, precipitate first, but are a metastable crystal phase.

(c) Accordingly, the addition of leucite seed crystals to the glassy material is essential to promote the precipitation of leucite crystals (metastable crystal phase), thereby maintaining the transparency of the glass-ceramic which is to be subjected to heated conditions for a long period of time, and stabilizing the coefficient of thermal expansion.

(d) It is clear that, when the leucite crystal-containing glass-ceramic obtained by the method of the invention is used as a porcelain, the ceramic coating layer formed in a series of fabrication steps for a dental prosthesis comprising application/buildup, fusion and cooling on a metal frame is substantially free of opacification and decrease in transparency.

EXAMPLE 2

Glassy material sample G2 (99 parts by weight) and leucite crystal sample L1 (1 part by weight) shown in Table 1 were uniformly mixed together, heat-treated for crystallization at 850° C. for 4 hours, cooled and pulverized to obtain a glass-ceramic powder according to the invention.

The obtained glass-ceramic powder had a leucite crystal content of 18 wt. %, and the leucite crystals had a mean particle size of 5 µm or smaller.

EXAMPLE 3

A glass-ceramic powder according to the invention was prepared by following the procedure of Example 2 except that the crystallization heat treatment at 850° C. was carried out for 3 hours.

The glass-ceramic powder had a leucite crystal content of 17.5 wt. %, and the leucite crystals had a mean particle size of 5 µm or smaller.

EXAMPLE 4

A glass-ceramic powder according to the invention was prepared by following the procedure of Example 2 except that 98 parts by weight of glassy material sample G2 and 2 parts by weight of leucite crystal sample L1 were used.

The obtained glass-ceramic powder had a leucite crystal content of 18.5 wt. %, and the leucite crystals had a mean particle size of 5 µm or smaller.

Comparative Example 2

A glass-ceramic powder was prepared by following the procedure of Example 2 except that only glassy material sample G2 (100 parts by weight) was used.

The obtained glass-ceramic powder had a leucite crystal content of 1.5 wt. %, and the leucite crystals had a mean particle size of 5 µm or smaller.

Comparative Example 3

A glass-ceramic powder was prepared by following the procedure of Comparative Example 2 except that the crystallization heat treatment at 850° C. was carried out for 8 hours.

The obtained glass-ceramic powder had a leucite crystal content of 10.5 wt. %, and the leucite crystals had a mean particle size of 5 µm or smaller.

Comparative Example 4

A glass-ceramic powder was prepared by following the procedure of Comparative Example 2 except that the crystallization heat treatment at 850° C. was carried out for 12 hours.

The obtained glass-ceramic powder had a leucite crystal content of 17.5 wt. %, and the leucite crystals had a mean particle size of 5 µm or smaller.

EXAMPLE 5

Glassy material sample G6 (99 parts by weight) and leucite crystal sample L1 (1 part by weight) shown in Table 1 were uniformly mixed together, heat-treated at 850° C. for 4 hours for crystallization, cooled and pulverized to obtain a glass-ceramic powder according to the invention.

The obtained glass-ceramic powder had a leucite crystal content of 35 wt. %, and the leucite crystals had a mean particle size of 5 µm or smaller.

Comparative Example 5

A glass-ceramic powder was prepared by following the procedure of Example 5 except that only glassy material sample G6 (100 parts by weight) was used.

The obtained glass-ceramic powder had a leucite crystal content of 4 wt. %, and the leucite crystals had a mean particle size of 5 µm or smaller.

EXAMPLE 6

Glassy material sample G3 (99 parts by weight) and leucite crystal sample L1 (1 part by weight) shown in Table 1 were uniformly mixed together, heat-treated at 850° C. for 2 hours for crystallization, cooled and pulverized to obtain a glass-ceramic powder according to the invention.

The obtained glass-ceramic powder had a leucite crystal content of 13 wt. %, and the leucite crystals had a mean particle size of 5 µm or smaller.

EXAMPLE 7

Glassy material sample G4 (99 parts by weight) and leucite crystal sample L1 (1 part by weight) shown in Table 1 were uniformly mixed together, heat-treated at 850° C. for 2 hours for crystallization, cooled and pulverized to obtain a glass-ceramic powder according to the invention.

The obtained glass-ceramic powder had a leucite crystal content of 22.5 wt. %, and the leucite crystals had a mean particle size of 5 µm or smaller.

EXAMPLE 8

A glass-ceramic powder according to the invention was prepared by following the procedure of Example 7 except that leucite crystal sample L2 shown in Table 1 was used in place of leucite crystal sample L1.

The obtained glass-ceramic powder had a leucite crystal content of 23.5 wt. %, and the leucite crystals had a mean particle size of 5 µm or smaller.

EXAMPLE 9

Glassy material sample G5 (99 parts by weight) and leucite crystal sample L1 (1 part by weight) shown in Table 1 were uniformly mixed together, heat-treated at 850° C. for 4 hours for crystallization, cooled and pulverized to obtain a glass-ceramic powder according to the invention.

The obtained glass-ceramic powder had a leucite crystal content of 21.5 wt. %, and the leucite crystals had a mean particle size of 5 μm or smaller.

Test Example 2

Each of the glass-ceramic powders (passed through 200 mesh) obtained in Examples 2 to 9 and Comparative Examples 2 to 5 was molded in the same manner as in Test Example 1, and made into a vacuum-fired body and 4-time refired body by following the firing schedules similar to those employed in Test Example 1. Then, the coefficients of thermal expansion of these fired and refired bodies were measured, and the appearances of the 4-time refired bodies were observed by the naked eye.

Table 2 presents these results.

TABLE 2

| | Coefficient of thermal expansion ($10^{-6}$/° C.) | | |
|---|---|---|---|
| | Vacuum-fired body | 4-time refired body | Appearance |
| Example 2 | 13.1 | 13.0 | Transparent |
| Example 3 | 13.0 | 13.1 | Transparent |
| Example 4 | 13.2 | 13.0 | Transparent |
| Example 5 | 16.5 | 16.5 | Transparent |
| Example 6 | 12.1 | 12.2 | Transparent |
| Example 7 | 14.0 | 14.1 | Transparent |
| Example 8 | 14.2 | 14.1 | Transparent |
| Example 9 | 13.8 | 13.8 | Transparent |
| Comp. Ex. 2 | 9.8 | 11.5 | Transparent |
| Comp. Ex. 3 | 11.6 | 12.8 | Opaque |
| Comp. Ex. 4 | 13.0 | 12.6 | Non-transparent |
| Comp. Ex. 5 | 10.3 | 13.5 | Transparent |

Table 2 reveals that the vacuum-fired bodies of the glass-ceramic powders obtained in Examples 2 to 9 had the desired coefficient of thermal expansion, and that the 4-time refired bodies of these glass-ceramic powders had a transparent appearance and substantially the same coefficients of thermal expansion as the corresponding vacuum-fired bodies.

In contrast, the vacuum-fired body and 4-time refired body of the glass-ceramic powder obtained in Comparative Example 2 did not have a desired coefficient of thermal expansion.

As to the glass-ceramic powder obtained in Comparative Example 3, its 4-time refired body had a desired high coefficient of thermal expansion, but was unsuitable for practical use owing to its opaque appearance.

The vacuum-fired body of the glass-ceramic powder obtained in Comparative Example 4 had a desire coefficient of thermal expansion, but the 4-time refired body of the glass-ceramic powder had a non-transparent appearance and thus was unsuitable for practical use.

The vacuum-fired body of the glass-ceramic powder obtained in Comparative Example 5 did not have a desired coefficient of thermal expansion.

Test Example 3

Tested were the mechanical and chemical characteristics (described hereinafter) of a translucent porcelain (Sample 1, $\alpha=13.8\times10^{-6}$/° C.) prepared by adding coloring agent (=opacifiers, pigments and fluorescent materials in the total amount of about 0.3 wt. % of the glass-ceramic powder weight) to the glass-ceramic powder obtained in Example 9, and four kinds of commercial translucent porcelains A to D as comparative samples.

The translucent porcelains used as samples have the following crystallographic characteristics.

Sample 1: A porcelain prepared by adding a small amount (about 0.3 wt. %) of coloring agent to the glass-ceramic powder obtained in Example 9 (leucite crystal content: 21.5 wt. %)

Sample 2 (commercial porcelain A): A porcelain with a leucite crystal content of 20.2 wt. %, which contains a small amount of coloring agent and a small amount of cristobalite as a different type of crystal Sample 3 (commercial porcelain B): A porcelain with a leucite crystal content of 18.3 wt. %, which contains a small amount of coloring agent and a small amount of high temperature-type Na—K sanidine as a different type of crystal Sample 4 (commercial porcelain C): A porcelain with a leucite crystal content of 18.9 wt. %, which contains a small amount of coloring agent and a small amount of high temperate-type Na—K sanidine as a different type of crystal Sample 5 (commercial porcelain D): A porcelain with a leucite crystal content of 7.4 wt. %, which contains a small amount of coloring agent Vickers Hardness Test pieces were prepared from Samples 1 to 5 in the same manner as in the thermal expansion test in Test Example 2. The test pieces were mirror finished, and the Vickers hardnesses Hv thereof were measured (load=2.9 N, loading time=15 seconds). The results are shown in Table 3 given hereinafter.

The test piece prepared from Sample 1 according to the invention had a sintered layer with a Vickers hardness Hv of 485, which is close to that of natural tooth enamel (about Hv 400). Thus, it is presumed that when a dental prosthesis fabricated using the porcelain according to the invention is used in the oral cavity, it causes less abrasion to natural teeth.

Also, the sintered layer of the test piece prepared from Sample 4 had a Vickers hardness relatively close to that of natural teeth.

On the other hand, the sintered layers of the test pieces prepared from commercially available Samples 2, 3 and 5 had a Vickers hardness Hv of 500 or more. Therefore, dental prostheses fabricated using these porcelains, when used in the oral cavity, are likely to abrade natural teeth.

Bending Strength

Using Sample 1 according to the invention and commercially available Samples 2 to 5, the three-point bending tests defined in JIS T 6516 were carried out. Table 3 shows the results.

Sample 1 according to the invention had a bending strength of 125 MPa, which is the highest in Table 3. Thus, a dental prosthesis fabricated using the porcelain according to the invention, when used in the oral cavity, is not liable to be damaged by occlusion pressure.

Contrastingly, commercially available Samples 2, 3 and 5 had low bending strengths. Thus, when dental prostheses fabricated using these porcelains are used in the oral cavity, they are likely to be broken.

In the porcelain according to the invention, the leucite crystal particles contained have an average particle size of 5 μm or smaller, and are uniformly dispersed through a porcelain. As a result, the porcelain according to the invention is free of concentration of bending stress, and has a high bending strength.

TABLE 3

| Sample | Hardness (Hv) | Bending strength (MPa) |
|--------|---------------|------------------------|
| 1 | 485 | 125 |
| 2 | 522 | 103 |
| 3 | 497 | 96 |
| 4 | 485 | 74 |
| 5 | 545 | 110 |

Solubility Test

Samples 1 to 5 were subjected to solubility tests in a 4% aqueous acetic acid solution, according to JIS T 6516.

All of the test pieces prepared from Samples 1 to 5 had 50% or less of the acceptable solubility defined in JIS T 6516 (0.05 wt. %).

INDUSTRIAL APPLICABILITY

In the present invention, leucite seed crystals synthesized in advance are used as a starting material, so that a leucite crystal-containing glass-ceramic with excellent high temperature stability can be easily prepared.

In the glass-ceramic obtained by the invention, different types of crystals such as Na—K feldspathic crystals start to precipitate long after the precipitation of leucite crystals reaches the saturation point. Therefore, during fusion-bonding to a metal frame, the glass-ceramic of the invention is substantially free of change in leucite crystal content and precipitation of other types of crystals such as Na—K feldspathic crystals, and thus has no substantial opacification.

Further, the coefficient of thermal expansion of the glass-ceramic obtained by the invention can be matched with that of a material of metal frame to be employed.

Therefore, when the glass-ceramic obtained by the invention is used as a porcelain for metal-ceramic dental restoration, the glass-ceramic does not substantially decrease in the coefficient of thermal expansion and is not substantially opacified, during fusion-bonding to a metal frame material.

The glass-ceramic obtained by the invention is highly transparent and has the excellent property of being freely colored, which is necessary to reproduce the color of natural teeth.

Since the glass-ceramic obtained by the invention contains at least 50 wt. % of glass phase, the glass-ceramic has excellent sintering properties and can be easily degassed during vacuum firing. Further, the glass-ceramic has excellent wettability on metal frames, and a high adhesion strength to frame materials.

The glass-ceramic obtained by the invention is also excellent in various mechanical characteristics (bending strength, Vickers hardness, etc.) and (chemical stability, etc.).

Moreover, even when a large proportion of opacifiers, inorganic coloring pigments, fluorescent materials or the like is added to a powder or controlled particle size powder of the glass-ceramic obtained by the invention, the resulting mixture is highly capable of being softened and fluidized by heating. This is because the glass-ceramic contains a large proportion of glass phase. Owing to this excellent property of being softened and fluidized, the amount of color pigment powders to be added can be adjusted in a wide range, so as to provide a porcelain for effectively concealing the color of a metal frame (opaque porcelain), or for effectively reproducing the color of natural teeth (dentine—dentine porcelain, enamel—enamel porcelain, margin formation—margin porcelain, and restoration and glazing—glaze porcelain).

What is claimed is:

1. A method for preparing a glass-ceramic containing leucite crystals, comprising the steps of:

mixing (1) a glassy material comprising 53 to 65 wt. % of $SiO_2$, 13 to 23 wt. % of $Al_2O_3$, 9 to 20 wt. % of $K_2O$ and 6 to 12 wt. % of $Na_2O$, and (2) synthetic leucite seed crystals comprising 53 to 64 wt. % of $SiO_2$, 19 to 27 wt. % of $Al_2O_3$ and 17 to 25 wt. % of $K_2O$; and heat-treating the mixture at 750 to 950° C. for 1 to 5 hours.

2. A method according to claim 1, wherein the synthetic leucite seed crystals (2) are at least one member selected from the group consisting of leucite crystals having a theoretical composition and leucite solid solutions containing a $SiO_2$ component dissolved therein.

3. A method according to claim 1, wherein the proportion of the synthetic leucite seed crystals (2) is 0.5 to 3 parts by weight per 100 parts by weight of the glassy material (1).

4. A method according to claim 2, wherein the proportion of the synthetic leucite seed crystals (2) is 1 to 2 parts by weight per 100 parts by weight of the glassy material (1).

5. A method according to claim 1, wherein the glassy material (1) contains at least one member selected from the group consisting of F and oxides of Li, Mg, Ca, Sr, B, P, Ti and Zr in a total proportion not exceeding 6 wt. %, and wherein the synthetic leucite seed crystals (2) contain at least one member selected from the group consisting of F and oxides of Li, Na, Rb, Mg, Ca, Sr, B, P, Ti and Zr in a total proportion not exceeding 3 wt. %.

6. A method according to claim 5, wherein the glassy material (1) contains at least one member selected from the group consisting of 0 to 2 wt. % of $Li_2O$, 0 to 3 wt. % of MgO, 0 to 3 wt. % of CaO, 0 to 2 wt. % of SrO, 0 to 3 wt. % of $B_2O_3$, 0 to 2 wt. % of $P_2O_5$ and 0 to 2 wt. % of F, and wherein the synthetic leucite seed crystals (2) comprise at least one member selected from the group consisting of 0 to 5 wt. % of $Rb_2O$, 0 to 2 wt. % of $Na_2O$, 0 to 2 wt. % of $Li_2O$, 0 to 3 wt. % of MgO and 0 to 3 wt. % of CaO.

7. A method according to claim 1, wherein the glassy material (1) comprises 61 to 65 wt. % of $SiO_2$, 14 to 17 wt. % of $Al_2O_3$, 11 to 16 wt. % of $K_2O$, 7 to 10 wt. % of $Na_2O$, 0.3 wt. % or less of $Li_2O$, 0.1 to 0.6 wt. % of MgO, 0.5 to 2 wt. % of CaO, 1 wt. % or less of SrO, 0.3 to 1.2 wt. % of $B_2O_3$, 2 wt. % or less of $TiO_2$, 0.5 wt. % or less of $ZrO_2$, 0.5 wt. % or less of $P_2O_5$ and 0.5 wt. % or less of F, in a total proportion not exceeding 6 wt. %.

8. A method according to claim 1, wherein both of the glassy material (1) and the synthetic leucite seed crystals (2) are powders having a particle size of 200 mesh or smaller.

9. A method according to claim 1, wherein the heat treatment is carried out at 800 to 900° C. for 1 to 5 hours.

10. A dental porcelain powder comprising, as a main ingredient, a powder of a glass-ceramic prepared by a method according to claim 1; the dental porcelain powder having a coefficient of thermal expansion which matches that of a dental alloy to be employed, and being colored so as to reproduce the color of natural teeth.

11. A metal-ceramic dental restoration fabricated using a porcelain powder according to claim 10.

* * * * *